US008917388B2

(12) United States Patent
Tenhunen et al.

(10) Patent No.: US 8,917,388 B2
(45) Date of Patent: Dec. 23, 2014

(54) MEASUREMENT OF RAMAN RADIATION

(75) Inventors: Jussi Tenhunen, Kiiminki (FI); Juha Kostamovaara, Oulu (FI)

(73) Assignees: Teknologian Tutkimuskeskus Vtt, Vtt (FI); Oulun Yliopisto, Oulu (FI)

( * ) Notice: Subject to any disclaimer, the term of this patent is extended or adjusted under 35 U.S.C. 154(b) by 83 days.

(21) Appl. No.: 13/501,966

(22) PCT Filed: Oct. 8, 2010

(86) PCT No.: PCT/FI2010/050782
§ 371 (c)(1),
(2), (4) Date: Apr. 13, 2012

(87) PCT Pub. No.: WO2011/045469
PCT Pub. Date: Apr. 21, 2011

(65) Prior Publication Data
US 2012/0194815 A1 Aug. 2, 2012

(30) Foreign Application Priority Data

Oct. 15, 2009 (FI) ..................................... 20096067

(51) Int. Cl.
*G01J 3/44* (2006.01)
*G01J 3/28* (2006.01)
*G01J 3/02* (2006.01)
*G01N 21/65* (2006.01)

(52) U.S. Cl.
CPC ............... *G01N 21/65* (2013.01); *G01J 3/2803* (2013.01); *G01J 3/02* (2013.01); *G01J 3/027* (2013.01); *G01J 3/44* (2013.01)
USPC ........................................................ 356/301

(58) Field of Classification Search
CPC .......................... G01N 21/65; G01N 2021/65
See application file for complete search history.

(56) References Cited

U.S. PATENT DOCUMENTS 5,048,959 A * 9/1991 Morris et al. ................. 356/301
5,418,797 A 5/1995 Bashkansky et al.
(Continued)

FOREIGN PATENT DOCUMENTS

EP 1035409 A2 9/2000
JP 8-509544 A 10/1996
(Continued)

OTHER PUBLICATIONS

Wahl et al., Optics Express, vol. 11, No. 26; Dec. 29, 2003 pp. 3583-3591.*

(Continued)

*Primary Examiner* — Tarifur Chowdhury
*Assistant Examiner* — Hina F Ayub
(74) *Attorney, Agent, or Firm* — Birch, Stewart, Kolasch & Birch, LLP.

(57) ABSTRACT

An apparatus comprises a plurality of detecting elements and a summer. Each detecting element receives and detects different bands of spectrum of Raman radiation formed in response to at least one optical excitation pulse directed to the object. The detecting elements and/or the summer receives a command to enable registration of detections in the detecting elements and a command to disable the registration during or after the Raman radiation. The summer registers separately the detections of the Raman radiation in at least two detecting elements for presenting data on the object on the basis of the detections.

28 Claims, 4 Drawing Sheets

(56) References Cited

U.S. PATENT DOCUMENTS

| | | |
|---|---|---|
| 5,821,547 A | 10/1998 | Talmi et al. |
| 5,864,397 A | 1/1999 | Vo-Dinh |
| 7,366,365 B2 | 4/2008 | Carver |
| 2002/0020819 A1 | 2/2002 | Wolleschensky et al. |
| 2003/0011765 A1 | 1/2003 | Xie et al. |
| 2003/0095893 A1 | 5/2003 | Luryi et al. |
| 2003/0206296 A1* | 11/2003 | Wolleschensky et al. .... 356/317 |
| 2004/0169854 A1 | 9/2004 | Vo-Dinh et al. |
| 2006/0231771 A1 | 10/2006 | Lee et al. |
| 2007/0167839 A1 | 7/2007 | Carver |
| 2007/0285658 A1 | 12/2007 | Claps et al. |
| 2008/0018890 A1 | 1/2008 | Maity et al. |
| 2008/0192232 A1 | 8/2008 | Ninomiya et al. |
| 2008/0225688 A1 | 9/2008 | Kowalski |
| 2008/0239307 A1 | 10/2008 | Talley et al. |
| 2008/0290259 A1 | 11/2008 | Mathewson et al. |
| 2012/0219029 A1 | 8/2012 | Scott et al. |

FOREIGN PATENT DOCUMENTS

| | | |
|---|---|---|
| JP | 9-159527 A | 6/1997 |
| JP | 2004-534232 A | 11/2004 |
| JP | 2005-524051 A | 8/2005 |
| JP | 2006-119152 A | 5/2006 |
| JP | 2006-519395 A | 8/2006 |
| JP | 2008-542706 A | 11/2008 |
| JP | 2010-517403 A | 5/2010 |
| WO | WO 2004/079351 A1 | 9/2004 |
| WO | WO 2005/015183 A1 | 2/2005 |
| WO | WO 2006/037248 A1 | 4/2006 |
| WO | WO 2006/126026 A1 | 11/2006 |
| WO | WO 2007/112099 A2 | 10/2007 |
| WO | WO 2008/097700 A2 | 8/2008 |
| WO | WO 2009/012222 A1 | 1/2009 |

OTHER PUBLICATIONS

Rech et al., "Photon-Timing Detector Module for Single-Molecule Spectroscopy With 60-ps Resolution", IEEE Journal of Selected Topics in Quantum Electronics, vol. 10, No. 4, Jul./Aug. 2004, pp. 788-795.

Schwartz et al., "A Single-Photon Avalanche Diode Array for Fluorescence Lifetime Imaging Microscopy", IEEE Journal of Solid-State Circuits, vol. 43, No. 11, Nov. 2008, pp. 2546-2557.

* cited by examiner

MEASUREMENT OF RAMAN RADIATION

This application is the national phase entry under 35 U.S.C. §371 of PCT International Application No. PCT/FI2010/050782, which has an international filing date of Oct. 8, 2010, which designated the United States of America, and which claims priority to Finnish Patent Application No. 2009-6069 filed Oct. 15, 2009, the entire contents of each of which are incorporated herein by reference.

FIELD

The invention relates to a measurement of Raman radiation.

BACKGROUND

Raman radiation results from inelastic scattering. When the monochromatic excitation radiation is directed to the object material, low-energy modes, such as vibration and rotation of molecules cause small deviations in the wavelength of the monochromatic radiation. Each deviation, in turn, is characteristic to each molecule in the material and hence molecules in the material can be identified.

The Raman radiation is notoriously difficult to measure since its intensity with respect to the excitation radiation is very low and it arrives at the detector almost simultaneously with the excitation radiation. Additionally, the excitation radiation gives rise to fluorescent radiation which is also simultaneous with the Raman radiation and whose lifetime is in nanosecond range.

Notch filters are usually employed to block the excitation radiation away as effectively as possible without attenuating other wavelengths excessively. The Raman radiation has also been separated from the fluorescent radiation using a gating device in front of the detector. For example, an optically controlled Kerr-gate may be placed in front of a detector. The Kerr-gate passes through optical radiation when it is in a transparent state and it blocks optical radiation when it is in a non-transparent state. The Kerr-gate can be switched to the transparent state using an optical control pulse from a laser, for example, and the Kerr-gate remains in the transparent state for the duration of the optical control pulse. At the end of the optical control pulse, the Kerr-gate returns to the non-transparent state. The Kerr-gate can be switched to the transparent state repeatedly by the optical control pulse for a desired period of time with an inaccuracy of a few picoseconds. In that way, both the excitation radiation and the fluorescent radiation can be suppressed effectively and the Raman radiation can be detected.

Instead of Kerr-gate, an image intensifier may correspondingly be placed in the front of the detector such as a CCD camera (Charge Coupled Device). The image intensifier which may also be called a wafer tube or a proximity-focused intensifier operates as a photomultiplier having more than a thousand volt over it. In addition to amplifying the received radiation, the image intensifier can be switched on and off with a frequency in a megahertz range and with a gate period of several hundreds on picoseconds.

However, there are problems related to the prior art. The duty cycle of a Kerr-gate is low, since the repetition rate of the transparent states of the Kerr-gate is typically less than one kilohertz, which makes the measurement unpractical. The operation of the Kerr-gate also needs high-energy optical pulses which drastically limit the energy of the optical pulses directed to the measured object from the same optical source. Correspondingly, the image intensifier has a problem due to a difficult and contradictious requirement of forming short pulses with well over 1000V. Background noise such as thermal noise and electron multiplication noise strongly limit the signal-to-noise ratio and disturb the measurements using the Kerr-gate and the image intensifier. Both measurement systems are also complicated, expensive and large such that they can only be used in laboratory.

Hence, there is a need for a better solution to measure Raman radiation.

BRIEF DESCRIPTION

According to an aspect of the present invention, there is provided an apparatus as specified in claim 1.

According to another aspect of the present invention, there is provided an apparatus as specified in claim 14.

According to another aspect of the present invention, there is provided a method as specified in claim 15.

The invention provides advantages. No additional gating devices are needed in front of the detector and the background noise can be limited. The measurement system is electrically controlled and capable of performing measurement of Raman radiation on-line. The repetition rate is mainly limited by the detecting elements.

LIST OF DRAWINGS

Embodiments of the present invention are described below, by way of example only, with reference to the accompanying drawings, in which FIG. 1 illustrates interaction of optical radiation and matter;

FIG. 2 presents an apparatus for measuring Raman radiation;

DESCRIPTION OF EMBODIMENTS

The following embodiments are exemplary. Although the specification may refer to "an", "one", or "some" embodiment(s), this does not necessarily mean that each such reference is to the same embodiment(s), or that the feature only applies to a single embodiment. Single features of different embodiments may also be combined to provide other embodiments.

Figure 1:
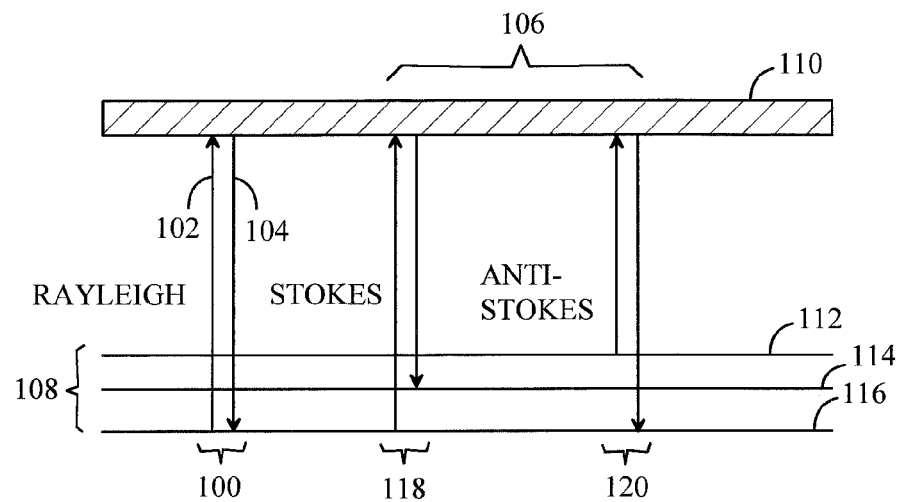

FIG. 1 shows a simplified principle of interaction between optical radiation and matter. Optical radiation can be considered to occupy a band from about 50 nm to about 500 µm. In Rayleigh scattering 100, absorption 102 of a photon has the same energy as emission 104 of a photon. In absorption of a photon, a total molecular energy jumps from a normal energy level 108 to an excited energy level 110. When the total molecular energy returns back from the excited level 110 to the normal level 108, a Rayleigh photon is emitted. The changes in the total molecular energy can be considered as shifts of electrons between different energy states in the molecule.

The normal energy level 108 may have several sub-levels 112, 114, 116 due to vibrational and/or rotational modes, for example, and in Raman scattering the total molecular energy may return to a different sub-level 112, 114, 116 than the sub-level it shifted from. When absorption 102 has a higher energy than emission 104, the emitted Raman radiation is based on Stokes scattering 118, and when the energies of absorption and emission are vice versa, the emitted Raman radiation is based on anti-Stokes scattering 120.

Figure 2:
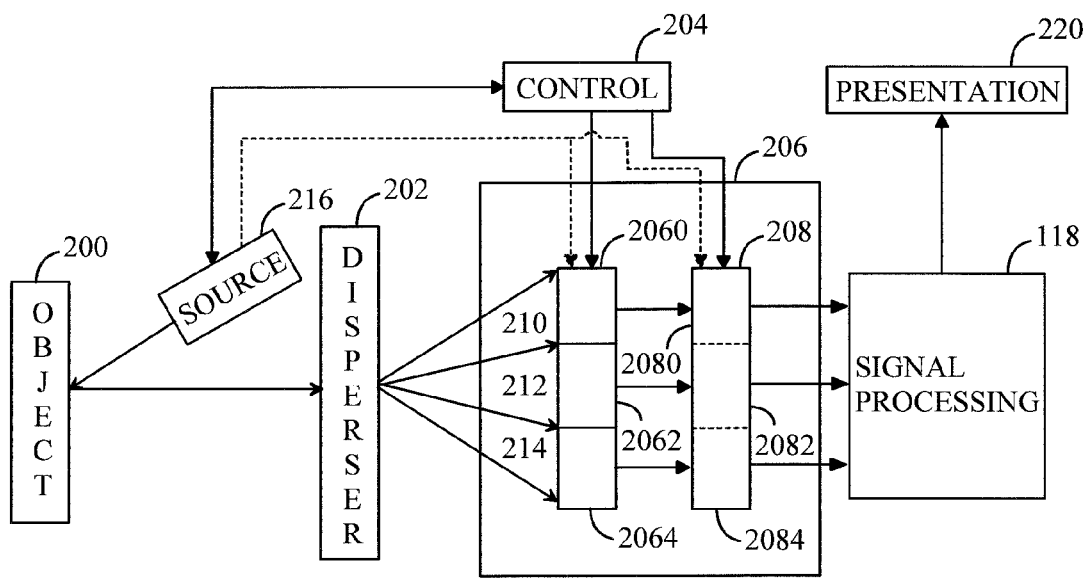

FIG. 2 presents a measurement device for measuring Raman radiation from an object 200. The measurement device may comprise a measuring unit 206 including a plurality of detecting elements 2060 to 2064 and a summer 208. Additionally, the measurement device may comprise a disperser 202 and a controller 204. The summer 208 may have summing elements 2080 to 2084 each of which is coupled with one detecting element 2060 to 2064 or the summer 208 may separately register detections in different detecting elements 2060 to 2064. The disperser 202 may be a spectrograph. The disperser 202 may receive optical radiation from the object 200 and the disperser 202 may disperse different wavelengths i.e. photons of different energies in different directions. The disperser 202 may comprise a grating or a prism for the dispersion of the optical radiation.

The disperser 202 may direct different bands 210 to 214 of the spectrum of the Raman radiation formed in response to at least one optical excitation pulse to different detecting elements 2060 to 2064 for reception. Each band 210 to 214 comprises at least one wavelength. In general in a band 210 to 214, the energies of photons are limited within a lower limit and an upper limit, the limits being known or predetermined. The disperser 202 may direct the Rayleigh radiation away from the detecting elements 2060 to 2064 and/or the Rayleigh radiation may be eliminated from the detection by strong attenuation of a notch filter or the like. To detect and register the Raman radiation properly, either the detecting elements 2060 to 2064 or the summer 208 can be time-gated. It is also possible to switch both the detecting elements 2060 to 2064 and the summer 208 on and off to enable time-gating and resetting the detecting elements 2060 to 2064.

The detecting elements 2060 to 2064 and/or the summer 208 may receive a command to enable registration of detection in the detecting elements 2060 to 2064, and to receive a command to disable the registration during or after the Raman radiation. The summer 208 then registers separately the detections of the Raman radiation in at least two detecting elements for presenting data on the object on the basis of the detections.

The controller 204 may be used to control the time-gating in or after the detecting elements 2060 to 2064. The controller 204 may electrically command the summer 208 to the registering state to enable the registration. The controller 204 may also electrically command the summer 208 to a non-registering state to disable the registration of detections from the detecting elements.

The controller 204 may electrically command each detecting element 2060 to 2064 to switch to a detecting state for detecting the Raman radiation of each excitation pulse separately and to electrically command each detecting element 2060 to 2064 to switch to a non-detecting state during or after the Raman radiation of each excitation pulse. The switching between detecting state and the non-detecting state may be performed regularly and/or repeatedly synchronously with the excitation pulses. Each detecting element 2060 to 2064 may detect photons in the band directed thereto after reception of a command to switch to the detecting state from the controller 204. Each detecting element 2060 to 2064 may receive a command to switch to the non-detecting state from the controller 204 and each detection element 2060 to 2064 stops detecting after the reception of the command. The controller 204 may also control the registration in the detecting elements 2060 to 2064.

The source 216 of optical radiation may also control the time-gating. The source 216 of optical radiation may directly command the detecting elements 2060 to 2064 and/or the summer 208 to enable registration. Correspondingly, the source 216 of optical radiation may directly command the detecting elements 2060 to 2064 and/or the summer 208 to disable registration after each optical excitation pulse.

Alternatively, the source 216 of optical radiation may transmit optical pulses independently without the control of the controller 204. In that case, the radiation source 216 may send a signal to the controller 204 each time it launches an optical pulse and the controller 204 may command the detecting elements 2060 to 2064 and/or the summer 208 to enable the registration. Correspondingly, the source 216 of optical radiation may send a signal to the controller 204 after each optical excitation pulse. In response to the signal from the source of optical radiation, the controller 204 may command the detecting elements 2060 to 2064 and/or the summer 208 to disable the registration.

The apparatus may additionally comprise optical radiation source 216 directed to the object 200. The controller 204 may command the optical radiation source 216 to output optical pulses to the object 200. The radiation source 216 may be a laser which can output short pulses at a desired wavelength. The laser may be a Nd:YAG (Neodymium doped Yttrium Aluminium Garnet) laser operating at 1064 nm wavelength, for example. The second harmonics (532 nm) or higher harmonics of the Nd:YAG laser could also be used.

Figure 3:
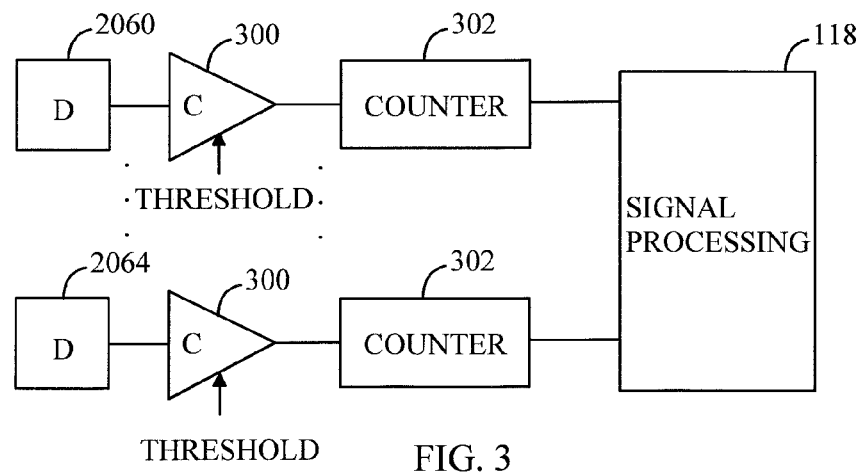
FIG. 3 illustrates signal processing for determination of detections.

As to FIG. 3, the summer 208 may comprise a comparator 300 and a counter 302 which each detecting element 2060 to 2064 is coupled to. The detecting elements 2060 to 2064 may be SPAD-arrays (Single Photon Avalanche Diode-arrays), for example. Each comparator 300 compares electric pulses generated by a detecting element 2060 to 2064 with a predetermined threshold. The threshold can be set to a suitable level on the basis of experiments, simulation or theory. Each counter 302 counts the number of the pulses crossing the predetermined threshold for determining the intensity of Raman radiation in each band.

Figure 4:
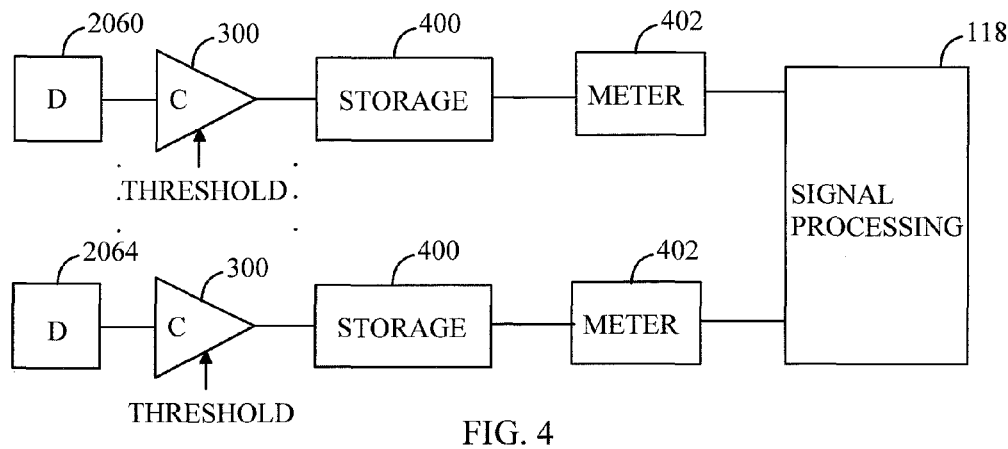
FIG. 4 illustrates different signal processing for determination of detections.

The summer 208 may alternatively comprise a charge storage 400 and a measuring unit 402 coupled to each detecting element 2060 to 2064 as shown in FIG. 4. Each detecting element 2060 to 2064 feeds a predetermined quantity of electric charge to a charge storage 400 in response to each detection. Each measuring unit 402 measures a property associated with the total charge in the charge storage 400 for determining the intensity of the Raman radiation associated in each band in the detecting elements 2060 to 2064. The intensity of the Raman radiation may be based on the number of detections in the detecting elements 2060 to 2064. The charge storage 400 may comprise at least one capacitor and the measuring unit 402 may be a circuit for measuring voltage over the at least one capacitor.

Figure 5:
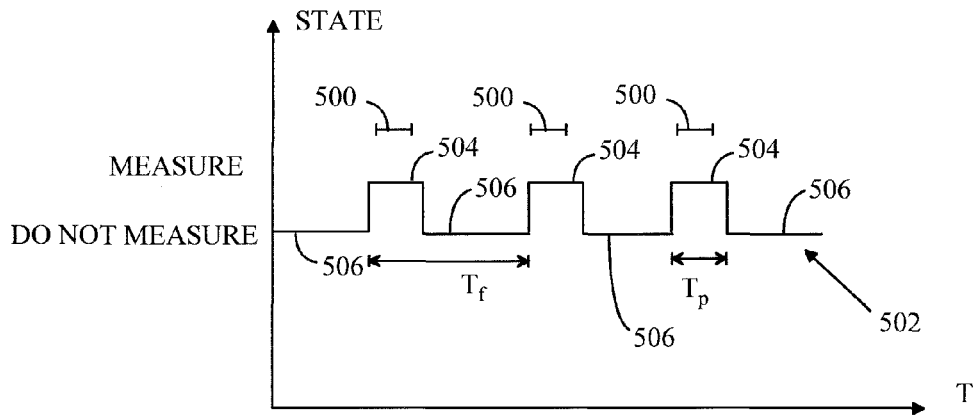
FIG. 5 illustrates timing of different operations.

FIG. 5 shows examples of periods of interactions 500 of the optical pulses with a detecting element 2060 to 2064 and the operational voltage 502 of the detecting elements 2060 to 2064. The horizontal axis is time T in an arbitrary scale and the vertical axis represents the state of measurement. The periods of the interactions 500 of the optical pulses with a detecting element 2060 to 2064 may take place in conjunction with the command of the controller 204 and/or the optical pulses of the source 216. The measuring unit 206 may be commanded to switch to the measuring state 504 before or at the rising edge of the interaction 500 of each optical pulse with a detecting element 2060 to 2064. The measuring unit 206 may be commanded to switch to the non-measuring state 506 after a predefined delay $T_p$ from the rising edge of the switch to the detecting state.

The switching between measuring state and non-measuring state may be performed in the following way, for example. The controller 204 may command the measuring unit 206 to switch to the detecting state 504 before or at the rising edge of the interaction 500 of each optical pulse with a detecting element 2060 to 2064. The controller 204 may also command the measuring unit 206 to switch to the non-detecting state 506 after a predefined delay $T_p$ from the rising edge of the switch to the detecting state. Instead of the controller 204, the source 216 of optical radiation may command the measuring unit 206 to switch to the measuring state and to the non-measuring state. In the measuring state, the registration of Raman radiation can be performed by registering the Raman photons. In such a case, the detecting elements 2060 to 2064 are in the detecting state and the summer 208 is in the registering state. In the non-measuring state, the registration of Raman radiation is stopped. In that case, either the detecting elements 2060 to 2064 are in the non-detecting state or the summer 208 is in the non-registering state. It is also possible that the detecting elements 2060 to 2064 are in the non-detecting state and the summer 208 are in the non-registering state during the non-measuring state.

In the non-measuring state, the summer 208 may be in the non-registering state but at least one detecting element 2060 to 2064 may be in a detecting state in order to measure the quantity and quality of background optical radiation. The background radiation may be due to fluorescence, daylight, illumination in the room etc. The quantity and quality of the background radiation may be used to correct the measurement results of Raman radiation and/or to guide the user to reduce or eliminate the deteriorating effects of the background optical radiation.

Figure 6:
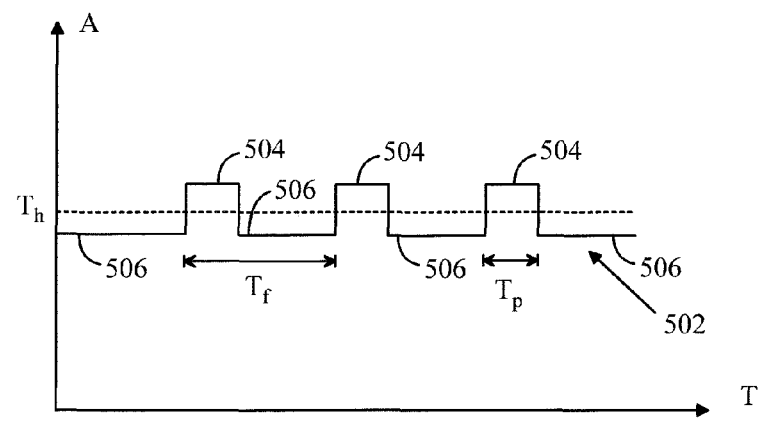
FIG. 6 illustrates behaviour of the operational voltage of the detecting elements.

FIG. 6 presents an example of operation of the measuring device. The horizontal axis is time T and the vertical axis is amplitude, both in an arbitrary scale. The operational voltage 502 fed to the detecting elements may be above zero and slightly below a threshold $T_h$ during the non-detection state 506 and the operation voltage may be set and kept above the threshold $T_h$ during the detection state 504. That makes the switching of the detecting elements from a state to a new state faster.

Alternatively or additionally to switching detecting elements 2060 to 2064 to non-detecting state, the controller 204 or the source 216 of optical radiation may command the summer 208 to stop the registration of electrical pulses from the detecting elements 2060 to 2064 after the predefined delay $T_p$ from the beginning of the registration or detection. Hence, the predefined delay $T_p$ can be considered to define a time window of the measuring state which may be a shorter period of time than the detecting state of the detecting elements 2060 to 2064.

The source 216 of optical radiation may use the time window shorter than, for example, 500 ps and a repetition rate of the time windows larger than, for example, a few kilohertz. The time window is the same as the delay $T_p$. The controller 204 or the source 216 of optical radiation may trigger the time window on and off synchronously with the exciting optical pulses. Each time window may also be shorter or longer than 500 ps. The frequency of the measuring states may not be limited at all. The frequency of the measuring states may be higher than 100 kHz for the detection of Raman radiation becomes faster with higher frequency. Hence, the frequency of measuring states may be above 1 MHz or even higher than 10 MHz. High frequency and narrow time windows are feasible because they are only limited by the characteristics of the detector. Both the frequency and the length of the time window may be fixed for the measurement or they may be adjusted alone or together during the measurement. The time window may be repeated regularly or irregularly.

Detecting Raman radiation in a pulsed mode filters the background noise and fluorescence out effectively, since outside the detecting or registration period no optical nor electric pulses are taken into account. That is an advantage over the prior art. The background noise may include thermal noise generated in the measuring system and background light (sunshine, lamplight etc.) hitting the detecting elements of the measuring system.

The time $T_f$ from a rising edge of a detecting state 504 to a next rising edge may then be, for example, 10 μs or less in average. The summer 208 may integrate the number and/or intensity of the detections in each detecting element 2060 to 2064 over a plurality of the detecting states 504.

Each detecting element 2060 to 2064 may be a photo diode such as an avalanche photo diode. Each detecting element 2060 to 2064 may alternatively be a single-photon detector which functions in a Geiger-mode. Such detectors transform each interaction with a photon to an electric pulse without an optical or electric time-gate, such as a Kerr-gate or an image intensifier in the front of the detector.

Figure 7:
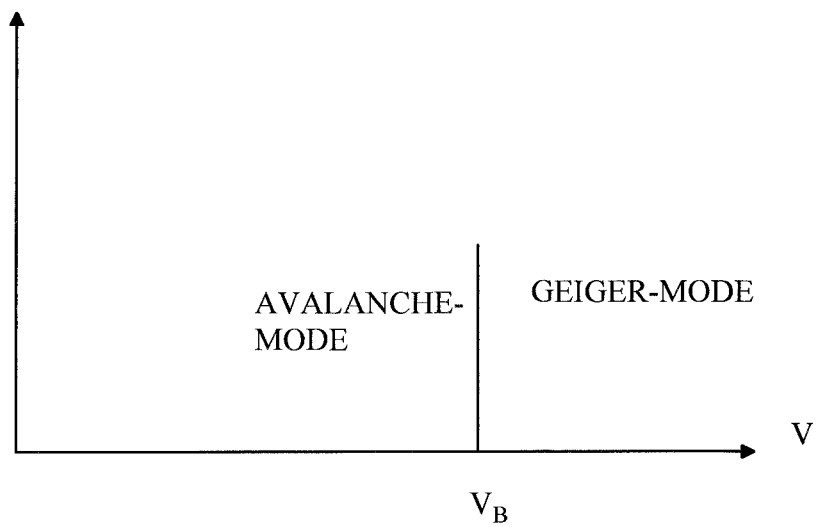
FIG. 7 illustrates different modes of operation of detecting elements.

FIG. 7 presents the avalanche-mode and the Geiger-mode. The diodes of both modes are made of semiconducting material and have a p-n junction which is reverse biased. In the avalanche-mode, the biasing voltage over the p-n junction is below a breakdown voltage $V_B$. The amplification in the avalanche-mode is the higher the closer the biasing voltage is to the breakdown voltage $V_B$. In the Geiger-mode, the biasing voltage over the p-n junction is above the breakdown voltage $V_B$. In the avalanche-mode, the intensity of the electrical output of the detecting means 106 depends linearly on the optical radiation i.e. the number of detected photons. To make the registration of Raman photons more effective, the Geiger-mode may be used. In the Geiger-mode, the response of the detecting elements 2060 to 2064 to optical radiation is non-linear and a single photon may cause the diode to output a strong electrical pulse for the summer 208.

In an embodiment, the detecting elements 2060 to 2064 are SPAD-arrays (Single Photon Avalanche Diode-arrays), for example. The electrical pulses generated by the detecting elements 2060 to 2064 on the basis of each detected photon may be further processed in the comparator 300 where the threshold may be set electrically. The threshold may be set, for instance, through quenching circuits 900 such as AQCs (Active Quenching Circuit).

The apparatus may comprise a signal processing unit 118 which determines numbers of the detections in at least two different groups of bands 210 to 214. A group of bands comprises at least one band. In an embodiment, the signal processing unit 118 determines detections associated with each band of the plurality of bands. Since each band is directed to one detecting element 2060 to 2064 and the summer 208 registers detections in each detecting element 2060 to 2064, the signal processing unit 118 may determine detections in each detecting element 2060 to 2064 or combine detections of several detecting elements in a desired manner. The signal processing unit 218 may form a distribution of the number and/or intensity of detections with respect to the detecting elements 206 which corresponds to the distribution of the number or intensity of detections with respect to a wavelength or energy of Raman photons. On the basis of the number of detections in at least two detecting elements 206, the signal processing unit 118 may determine a property associated with the object.

In an embodiment, the signal processing unit 118 may identify a material in the object on the basis of comparison of the numbers of detections in different detecting elements 2060 to 2064.

In an embodiment, the signal processing unit 118 may determine concentration of a material in the object on the basis of the number of detections in different detecting elements 2060 to 2064.

The apparatus may comprise a presentation unit 220 which may be a display for presenting graphical and/or alphanumeric data. The presentation unit 220 may be a part of a user interface which may be used to input values for various adjustable parameters such as repetition frequency of the optical pulses, duration of the optical pulses, duration of the measuring state (delay $T_p$) etc.

Instead of the number of the detections, the intensity of the Raman radiation in different detection elements 2060 to 2064 may be determined. The determined intensities and/or distribution of the determined intensities with respect to the detecting elements 2060 to 2064 may be used in the determination of material in the object 200 and/or the concentration of at least one material.

Figure 8:
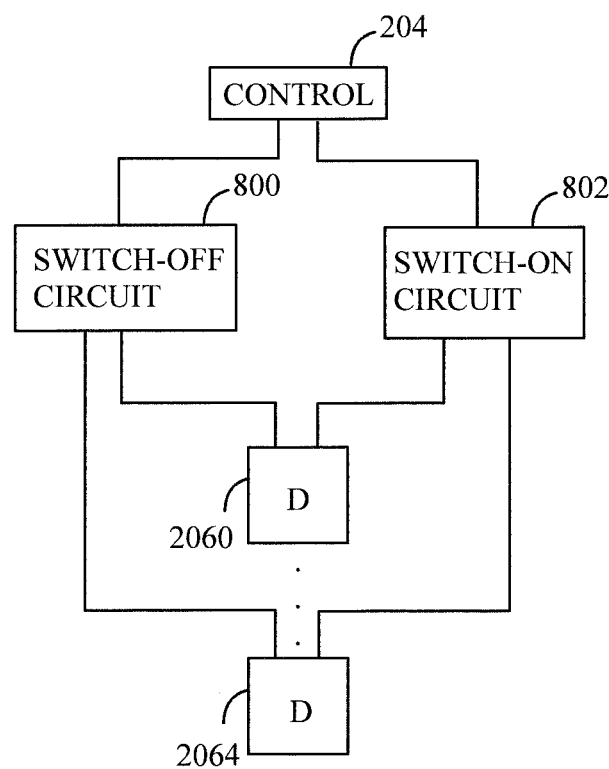
FIG. 8 illustrates circuits driving the detecting elements.

As shown in FIG. 8, the apparatus may comprise a switch-off circuit 800 which actively drives each detecting element 2060 to 2064 to the non-detecting state at the end of each measuring state. However, the switch-off circuit 800 may not be needed. Instead of switching each detecting element 2060 to 2064 to non-detecting state, the registration of electrical pulses of detecting elements may be stopped in the counter 302 or in the storage 400 under control of the controller 204 for a controlled period of time associated to a repetition of the time window of the delay $T_p$.

The apparatus may comprise a switch-on circuit 802 which actively drives each detecting element 2060 to 2064 to the detecting state. The switch-on circuit 802 fastens the switching on the detecting elements 2060 to 2064.

Figure 9:
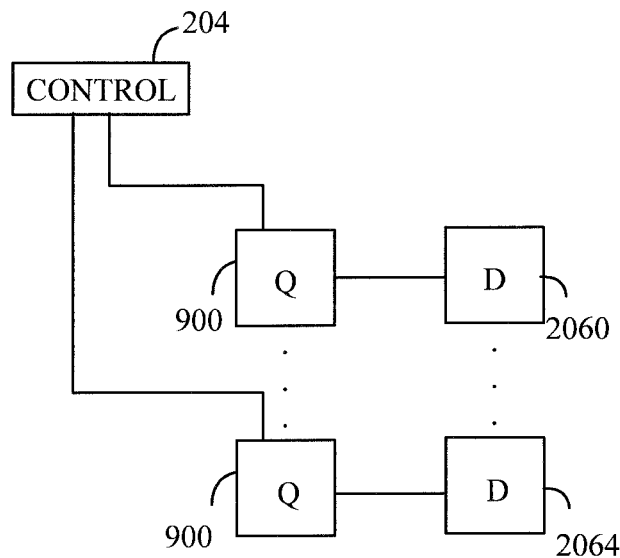
FIG. 9 illustrates a quenching circuit.

FIG. 9 presents a quenching circuit 900 in an embodiment where detecting elements 2060 to 2064 are used in the Geiger-mode. When a photon hits a detecting element in a Geiger-mode, the detecting element has a dead time after each detection, during which the detecting element is not capable of detecting a new photon. The dead time can be shortened or eliminated using a quenching circuit 900 which may be active or passive. A passive quenching circuit may be as simple as a resistor coupled to the detecting element. The passive circuit causes self-quenching of the detecting element. An active quenching circuit comprises at least one active component like a transistor. The active quenching circuit detects the breakdown of the detecting element and outputs a suitably timed electrical quenching pulse to the detecting element for recovering the detecting element quickly back to the detecting state.

The use of the switch-off circuit 800, the switch-on circuit 802 and/or a quenching circuit 900 enable the use of a short time window the length of which may be, for example, 100 ps for the detections. A detection of background noise, for example, 1 ns before Raman radiation hitting a detecting element prevents the detecting element from detecting the Raman radiation during the dead time. By the use of the switch-on circuit 802 and the switch-off circuit 800, such an effect of the dead time can be avoided, since the detecting element may be kept switched in a non-detecting state before the impact of the Raman radiation.

The controller 204 may be a rather simple electronic circuit particularly in the case when the measuring state of the detecting elements is triggered on and off synchronously with the excitation optical pulses of the optical radiation source 216. However, the controller 204 and the signal processing unit 118 may also be implemented as an electronic digital computer, which may comprise a working memory (RAM), a central processing unit (CPU), and a system clock. The CPU may comprise a set of registers, an arithmetic logic unit, and a control unit. The program instructions may be coded by a programming language.

The computer program or programs, which is used for controlling the detecting elements 2060 to 2064 and the optical radiation source 216 and performing the signal processing, may be stored in some sort of carrier, which may be any entity or device capable of carrying the program. Such carriers include a record medium, computer memory, read-only memory, electrical carrier signal, telecommunications signal, and software distribution package, for example. Depending on the processing power needed, the computer program may be executed on a single electronic digital computer or it may be distributed amongst a number of computers.

The electronic components of the apparatus may also be implemented as one or more integrated circuits, such as application-specific integrated circuits ASIC. Other hardware embodiments are also feasible, such as a circuit built of separate logic components. A hybrid of these different implementations is also feasible. When selecting the method of implementation, a person skilled in the art will consider the requirements set for the size and power consumption of the apparatus, necessary processing capacity, production costs, and production volumes, for example.

Figure 10:
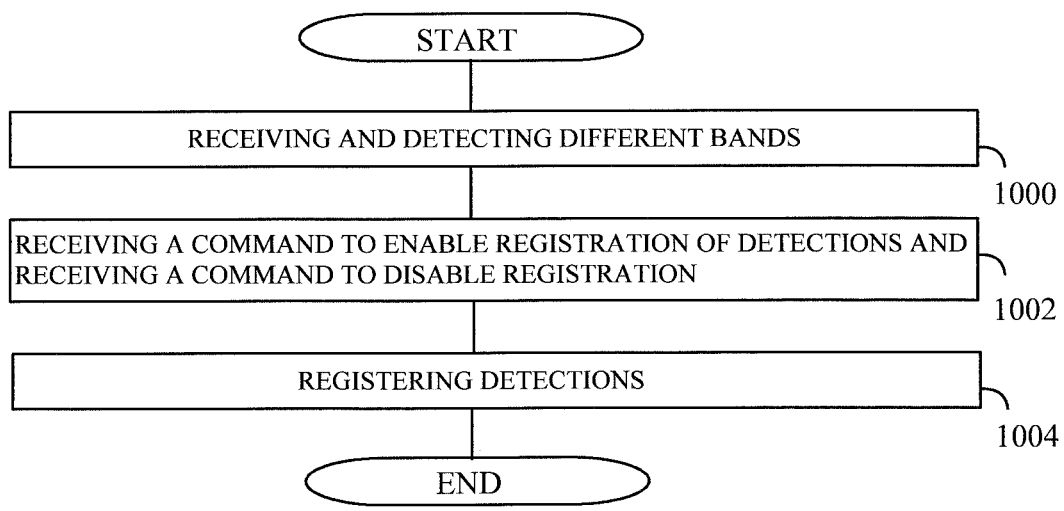
FIG. 10 shows a flow chart of the method.

Next, a method will be described with reference to FIG. 10. In step 1000, different bands of spectrum of Raman radiation formed in response to at least one excitation pulse are received in different detecting elements. In step 1002, receiving, in the detecting elements and/or a summer, a command to enable registration of the Raman radiation and a command to disable the registration of the Raman-radiation during or after the Raman radiation. In step 1004, the detections of Raman radiation for each excitation pulse in at least two detecting elements are separately registered in the summer for presenting data on the object on the basis of the detections.

The apparatus and the method may be applied in various processes, which may be performed in a medical and paper industry, for example. An effective molecule and/or its presence may be determined and its concentration in the medium may also be determined.

The apparatus is suitable for field experiments and on-line measurements due to at least one of the following: low background noise, fluorescence suppression, simplicity, small size, reliability and low cost.

It will be obvious to a person skilled in the art that, as technology advances, the inventive concept can be implemented in various ways. The invention and its embodiments are not limited to the examples described above but may vary within the scope of the claims.

The invention claimed is:

1. An apparatus for measuring Raman radiation from an object, the apparatus comprising: an array having a plurality of detecting elements and a summer;

each detecting element being configured to function as a single-photon detector of a Geiger-mode and receive and detect different bands of spectrum of Raman radiation formed in response to at least one optical excitation pulse directed to the object;

the detecting elements and/or the summer being configured to receive a command to enable registration of detections in the detecting elements, and to receive a command to disable the registration during or after the Raman radiation; and the summer being configured to register separately the detections of the Raman radiation in at least two detecting elements and integrate the number of detections for presenting data on the object on the basis of the detections.

2. The apparatus of claim 1, wherein the summer is configured to switch to a registering state in response to the command to enable the registration, and the summer is configured to switch to a non-registering state in response to the command to disable registration during or after the Raman radiation.

3. The apparatus of claim 1, wherein each detecting element is configured to switch to a detecting state for detecting the Raman radiation in response to the command to enable registration and each detecting element is configured to switch to a non-detecting state after the Raman radiation in response to the command to disable registration.

4. The apparatus of claim 1, wherein the apparatus comprises a controller configured to command the source of optical radiation configured to output optical pulses to the object, to command each detecting element to switch to the detecting state during or after an estimated interaction of each optical pulse with a detecting element, and to command each detecting element to switch to the non-detecting state after a predefined delay after the switch to the detecting state, the detecting elements and/or the summer to enable the registration, and the detecting elements and/or the summer to disable the registration.

5. The apparatus of claim 1, wherein the apparatus comprises a source of optical radiation configured to output optical pulses to the object, and command the detecting elements and/or the summer to enable registration, and command the detecting elements and/or the summer to disable registration.

6. The apparatus of claim 1, wherein the apparatus comprises a disperser configured to receive Raman radiation from the object and to direct different bands of a spectrum of Raman radiation to different detecting elements.

7. The apparatus of claim 1, wherein the apparatus is configured to measure detections of the Raman radiation of each excitation pulse in a time window shorter than 500 ps and to repeat the measurements with a frequency higher than 100 kH synchronously with the excitation pulses by enabling and disabling the registrations, and the summer is configured to integrate the number of the detections over a plurality of the time windows.

8. The apparatus of claim 1, wherein the summer comprises a comparator and a counter coupled to each detecting element, the comparator being configured to compare electric pulses generated by a detecting element coupled therewith with a predetermined threshold, the counter being configured to count the number of the pulses crossing the threshold for determining the number of the detections in each band.

9. The apparatus of claim 1, wherein the summer comprises a charge storage and a measuring unit coupled to each detecting element, the charge storage being coupled to a detecting element configured to feed a predetermined quantity of electric charge to the charge storage in response to each detection and the measuring unit being configured to measure a property associated with the total charge in the charge storage for determining the number of the detections in each band.

10. The apparatus of claim 1, wherein each detecting element is a single-photon detection element that functions in a Geiger-mode.

11. The apparatus of claim 1, wherein the apparatus comprises a signal processing unit configured to determine numbers of the detections in at least two bands and to determine a property associated with the object on the basis of the numbers of detections in different detecting elements.

12. The apparatus of claim 11, wherein the signal processing unit is configured to identify a material in the object on the basis of comparison of the numbers of detections in different bands.

13. The apparatus of claim 11, wherein the signal processing unit is configured to determine concentration of a material in the object on the basis of the number of detections in the detecting elements.

14. A method for measuring Raman radiation from an object, the method comprising:

receiving and detecting, in different detecting elements of an array, single-photons of different bands of spectrum of Raman radiation formed in response to at least one excitation pulse in a Geiger-mode;

receiving, in the detecting elements and/or a summer, a command to enable registration of detections in the detecting elements and a command to disable registration during or after the Raman radiation; and registering, in the summer, separately the detections of the Raman radiation in at least two detecting elements and integrating the number of detections for presenting data on the object on the basis of the detections.

15. The method of claim 14, the method further comprising directing different bands of spectrum of the Raman radiation to different detecting elements by a disperser.

16. The method of claim 14, the method further comprising switching the summer to a registration state of the Raman radiation in response to the command to enable registration and switching the summer to a non-registering state in response to the command to disable registration.

17. The method of claim 14, the method further comprising switching the detection elements to a detecting state of the Raman radiation in response to the command to enable registration and switching the detection elements to a non-detecting state in response to the command to disable registration.

18. The method of claim 14, the method further comprising commanding, by the source of optical radiation, each detecting element and/or the summer to enable the registration, and each detecting element and/or the summer to disable the registration.

19. The method of claim 14, the method further comprising commanding the source of optical radiation to output optical pulses to the object, each detecting element and/or the summer to enable the registration, and each detecting element and/or the summer to disable the registration.

20. The method of claim 14, the method further comprising setting a time window shorter than 500 ps for the Raman radiation of each excitation pulse and repeating the measurements with a frequency higher than 100 kHz by enabling and disabling the registration, and integrating the number of the detections over a plurality of the time windows.

21. The method of claim 14, the method further comprising comparing, by a comparator, electric pulses generated by a detecting element coupled thereto with a predetermined threshold, and counting, by a counter, the number of the pulses crossing the threshold for determining the number of the detections in each band.

22. The method of claim 14, the method further comprising in the summer feeding, by a detecting element, a predetermined quantity of electric charge to a charge storage in response to each detection, and measuring, by a measuring unit, a property associated with the total charge in the charge storage for determining the number of the detections in a band.

23. The method of claim 14, wherein each detecting element is a single-photon detection element configured to function in a Geiger-mode.

24. The method of claim 14, the method further comprising determining, by a signal processing unit, numbers of the detections in at least two detecting elements and determining a property associated with the object on the basis of the numbers of detections in different detecting elements.

25. The method of claim 24, the method further comprising identifying, by the signal processing unit, a material in the object on the basis of comparison of the numbers of detections in different detecting elements.

26. The method of claim 24, the method further comprising determining, by the signal processing unit, concentration of a material in the object on the basis of the number of detections in detecting elements.

27. The apparatus of claim 1, wherein a time window between the switching to the registering state and the switching to the non-registering state being shorter than 500 ps.

28. The method of claim 14, wherein a time window between the switching to the registering state and the switching to the non-registering state being set shorter than 500 ps.

* * * * *